(12) United States Patent  
Maruhata

(10) Patent No.: US 10,973,700 B2
(45) Date of Patent: *Apr. 13, 2021

(54) ABSORBENT-ARTICLE SHEET MEMBER MANUFACTURING APPARATUS

(71) Applicant: LIVEDO CORPORATION, Ehime (JP)

(72) Inventor: Kazuya Maruhata, Tokushima (JP)

(73) Assignee: LIVEDO CORPORATION, Ehime (JP)

( * ) Notice: Subject to any disclaimer, the term of this patent is extended or adjusted under 35 U.S.C. 154(b) by 408 days.

This patent is subject to a terminal disclaimer.

(21) Appl. No.: 16/013,378

(22) Filed: Jun. 20, 2018

(65) Prior Publication Data

US 2018/0296400 A1 Oct. 18, 2018

Related U.S. Application Data

(63) Continuation of application No. 14/787,354, filed as application No. PCT/JP2014/065621 on Jun. 12, 2014, now Pat. No. 10,117,789.

(30) Foreign Application Priority Data

Jul. 16, 2013 (JP) .................................. 2013-147370

(51) Int. Cl.
 *A61F 13/15* (2006.01)
(52) U.S. Cl.
 CPC .. *A61F 13/15764* (2013.01); *A61F 13/15658* (2013.01); *A61F 2013/15821* (2013.01)
(58) Field of Classification Search
 None
 See application file for complete search history.

(56) References Cited

U.S. PATENT DOCUMENTS

| 2002/0115969 A1 | 8/2002 | Maeda et al. |
| 2006/0021695 A1 | 2/2006 | Blessing et al. |

(Continued)

FOREIGN PATENT DOCUMENTS

| JP | 2005-59579 | 3/2005 |
| JP | 4795612 | 10/2011 |

(Continued)

OTHER PUBLICATIONS

International Search Report dated Aug. 26, 2014 in International Application No. PCT/JP2014/065621.

(Continued)

*Primary Examiner* — Barbara J Musser
(74) *Attorney, Agent, or Firm* — Wenderoth, Lind & Ponack, L.L.P.

(57) ABSTRACT

An absorbent sheet manufacturing apparatus has a particle collision surface (224) that extends downward from a cylinder outer surface (211) in between the lowermost part of a supply cylinder (21) and a second sheet conveying roller (41). Some of the particles emitted forward in the rotation direction of the supply cylinder (21) from recessed supply portions (212) that have passed a first cover part (221) collide with the particle collision surface (224), and the colliding particles are guided by the particle collision surface (224) onto a first sheet member (91). This suppresses direct collision of particles emitted from the supply cylinder (21) with a second sheet member (92) on the second sheet conveying roller (41). Scattering of particles that have collided with the second sheet member (92) around the first sheet member (91) and the second sheet member (92) is thus suppressed.

19 Claims, 9 Drawing Sheets

(56) References Cited

U.S. PATENT DOCUMENTS

2006/0048880 A1     3/2006   Blessing et al.
2006/0278335 A1   12/2006   Moriura et al.
2014/0008024 A1     1/2014   Ogasawara et al.

FOREIGN PATENT DOCUMENTS

| JP | 2012-147957 | | 8/2012 | |
|---|---|---|---|---|
| JP | 2013-17563 | | 1/2013 | |
| JP | 2013017563 A | * | 1/2013 | ......... B32B 37/0053 |
| WO | 2013/008431 | | 1/2013 | |

OTHER PUBLICATIONS

International Preliminary Report on Patentability dated Jan. 19, 2016 in International Application No. PCT/JP2014/065621.

* cited by examiner

ABSORBENT-ARTICLE SHEET MEMBER MANUFACTURING APPARATUS

CROSS-REFERENCE TO RELATED APPLICATIONS

This application is a continuation of and claims benefit to U.S. application Ser. No. 14/787,354, filed Oct. 27, 2015, now U.S. Pat. No. 10,117,789.

TECHNICAL FIELD

The present invention relates to an absorbent-article sheet member manufacturing apparatus.

BACKGROUND ART

Absorbent articles such as absorbent pads for light incontinence that are used by being attached to the inner sides of disposable diapers conventionally use absorbent sheets produced by sandwiching and fixing particles of a highly absorbent resin or the like between two sheet members of a nonwoven fabric or the like. In manufacturing such absorbent sheets, particles of the highly absorbent resin are supplied onto one sheet member that is conveyed at a constant speed, and then the other sheet member is layered on and bonded to the one sheet member.

An absorbent-article sheet member manufacturing apparatus disclosed in Japanese Patent Application Laid-Open No. 2013-17563 (Document 1) includes a cylinder part in which a plurality of concave portions to be filled with highly absorbent resin particles are formed in the outer surface, a first sheet conveying roller for conveying a first sheet member in the vicinity of the lowermost part of the cylinder part, and a second sheet conveying roller that is disposed forward of the lowermost part of the cylinder part in the rotation direction and is for conveying a second sheet member and layering the second sheet member on the first sheet member. In the apparatus, particles are ejected from concave portions that pass the vicinity of the lowermost part of the cylinder part, and some of the ejected particles collide with the second sheet member on the second sheet conveying roller and then fall on the first sheet member. The outer surface of the second sheet conveying roller has a plurality of grooves extending fully circumferentially. These grooves absorb the impact of particles that collide with the second sheet member on the second sheet conveying roller, thus suppressing scattering of particles in the surroundings.

With the absorbent-article sheet member manufacturing apparatus of Document 1, there are cases in which particles that have collided with the second sheet member on the second sheet conveying roller bounce back upwardly or laterally and scatter around the first sheet member and the second sheet member. In particular, particles that have collided with the second sheet member at positions higher than the central axis of the second sheet conveying roller are more likely to bounce back to positions higher than where they collided and scatter in the surroundings.

SUMMARY OF INVENTION

The present invention is intended for an absorbent-article sheet member manufacturing apparatus, and it is an object of the present invention to suppress scattering of particles in the surroundings.

An absorbent-article sheet member manufacturing apparatus according to the present invention includes a supply cylinder having a cylinder outer surface that is a generally cylindrical surface centered on a rotation axis pointing in a horizontal direction, having a plurality of supply holes that are a plurality of recessed supply portions arrayed in a circumferential direction in the cylinder outer surface, and for rotating about the rotation axis in a predetermined rotation direction, a particle filling part for housing particles of an absorbent material or a deodorant material above the supply cylinder and successively filling the plurality of supply holes with particles through a particle filling opening that faces the cylinder outer surface, a half cover part that extends from the particle filling opening to a lower part of the supply cylinder in the rotation direction to cover part of the cylinder outer surface of the supply cylinder, a first sheet conveying roller disposed below the supply cylinder and in close proximity to a lowermost part of the supply cylinder, having a first roller outer surface that is a generally cylindrical surface centered on a first central axis pointing in an axial direction that is parallel to the rotation axis, and for rotating about the first central axis in an opposite direction to the rotation direction to convey a first sheet member that is a continuous sheet along the first roller outer surface, a second sheet conveying roller disposed forward of the lowermost part of the supply cylinder in the rotation direction and in close proximity to the supply cylinder and the first sheet conveying roller, having a second roller outer surface that is a generally cylindrical surface centered on a second central axis pointing in the axial direction, and for rotating about the second central axis in the same direction as the rotation direction to convey a second sheet member that is a continuous sheet along the second roller outer surface and to layer the second sheet member on the first sheet member, a particle collision surface that extends from the cylinder outer surface in between the lowermost part of the supply cylinder and the second sheet conveying roller, and for colliding with some of the particles that are emitted forward in the rotation direction of the supply cylinder from a supply hole that has passed the half cover part and guiding the colliding particles onto the first sheet member, and a sheet bonding part for bonding the first sheet member and the second sheet member to each other. This configuration suppresses scattering of particles in the surroundings.

Another absorbent-article sheet member manufacturing apparatus according to the present invention includes a supply cylinder that is a generally cylindrical member centered on a rotation axis pointing in a horizontal direction, having a particle-housing space in which part of an internal space is for housing particles of an absorbent material or a deodorant material, having a plurality of supply holes that are a plurality of through holes arrayed in a circumferential direction, and for rotating about the rotation axis in a predetermined rotation direction to fill a supply hole that faces particles housed in the particle-housing space among the plurality of supply holes, with particles, a half cover part that extends from a lower part of the supply cylinder in an opposite direction to the rotation direction to cover part of a cylinder outer surface that is an outer surface of the supply cylinder, a separating part that covers part of an inner surface of the supply cylinder to separate the particle-housing space and a supply hole at the lower part of the supply cylinder, a first sheet conveying roller disposed below the supply cylinder and in close proximity to a lowermost part of the supply cylinder, having a first roller outer surface that is a generally cylindrical surface centered on a first central axis pointing in an axial direction that is parallel to the rotation axis, and for rotating about the first central axis in an opposite direction to the rotation direction to convey a first sheet member that is a continuous sheet along the first roller outer surface, a second sheet conveying roller disposed forward of the lowermost part of the supply cylinder in the rotation direction and in close proximity to the supply cylinder and the first sheet conveying roller, having a second roller outer surface that is a generally cylindrical surface centered on a second central axis pointing in the axial direction, and for rotating about the second central axis in the same direction as the rotation direction to convey a second sheet member that is a continuous sheet along the second roller outer surface and to layer the second sheet member on the first sheet member, a particle collision surface that extends from the cylinder outer surface in between the lowermost part of the supply cylinder and the second sheet conveying roller, and for colliding with some of the particles that are emitted forward in the rotation direction of the supply cylinder from a supply hole that has passed the half cover part and guiding the colliding particles onto the first sheet member, and a sheet bonding part for bonding the first sheet member and the second sheet member to each other. This configuration suppresses scattering of particles in the surroundings.

In a preferred embodiment of the present invention, the particle collision surface is an inclined surface that is inclined forward in the rotation direction with respect to a vertically downward direction.

In another preferred embodiment of the present invention, the particles that are emitted from the supply hole that has passed the half cover part toward a space between a lower end of the particle collision surface and the first sheet member on the first sheet conveying roller collide directly with the second sheet member on the second sheet conveying roller at a position below the second central axis of the second sheet conveying roller.

In another preferred embodiment of the present invention, a lower end of the particle collision surface is located below or at the same position as the second central axis of the second sheet conveying roller in an up-down direction.

In another preferred embodiment of the present invention, the absorbent-article sheet member manufacturing apparatus further includes a pair of side wall parts disposed on both sides, in the axial direction, of a group of supply holes in the cylinder outer surface that are exposed between a lower end of the half cover part and the particle collision surface. Each side wall part of the pair is provided in close proximity to the cylinder outer surface and continuously from the lower end of the half cover part to the particle collision surface, and extends downward from the cylinder outer surface.

More preferably, a lower end of each side wall part of the pair includes an inclined portion that is inclined downward as the inclined portion extends from the particle collision surface toward the half cover part.

In another preferred embodiment, the plurality of supply holes include a plurality of supply hole rows, each supply hole row being a group of supply holes that are arrayed in the circumferential direction at the same position in the axial direction. The absorbent-article sheet member manufacturing apparatus further includes a partition part provided between the pair of side wall parts and continuously from the lower end of the half cover part to the particle collision surface. The partition part is provided in close proximity to the cylinder outer surface while facing a portion of the cylinder outer surface between the plurality of supply hole rows, and extends downward from the cylinder outer surface.

More preferably, a lower end of the partition part includes an inclined portion that is inclined downward as the inclined portion extends from the particle collision surface toward the half cover part.

In another preferred embodiment, the half cover part, the particle collision surface, and the pair of side wall parts are included in an integral member.

In another preferred embodiment, the second central axis of the second sheet conveying roller is located at a position that is forward of the lowermost part of the supply cylinder in the rotation direction and between the cylinder outer surface and the first roller outer surface that face each other in an up-down direction.

These and other objects, features, aspects and advantages of the present invention will become more apparent from the following detailed description of the present invention when taken in conjunction with the accompanying drawings.

DESCRIPTION OF EMBODIMENTS

Figure 1:
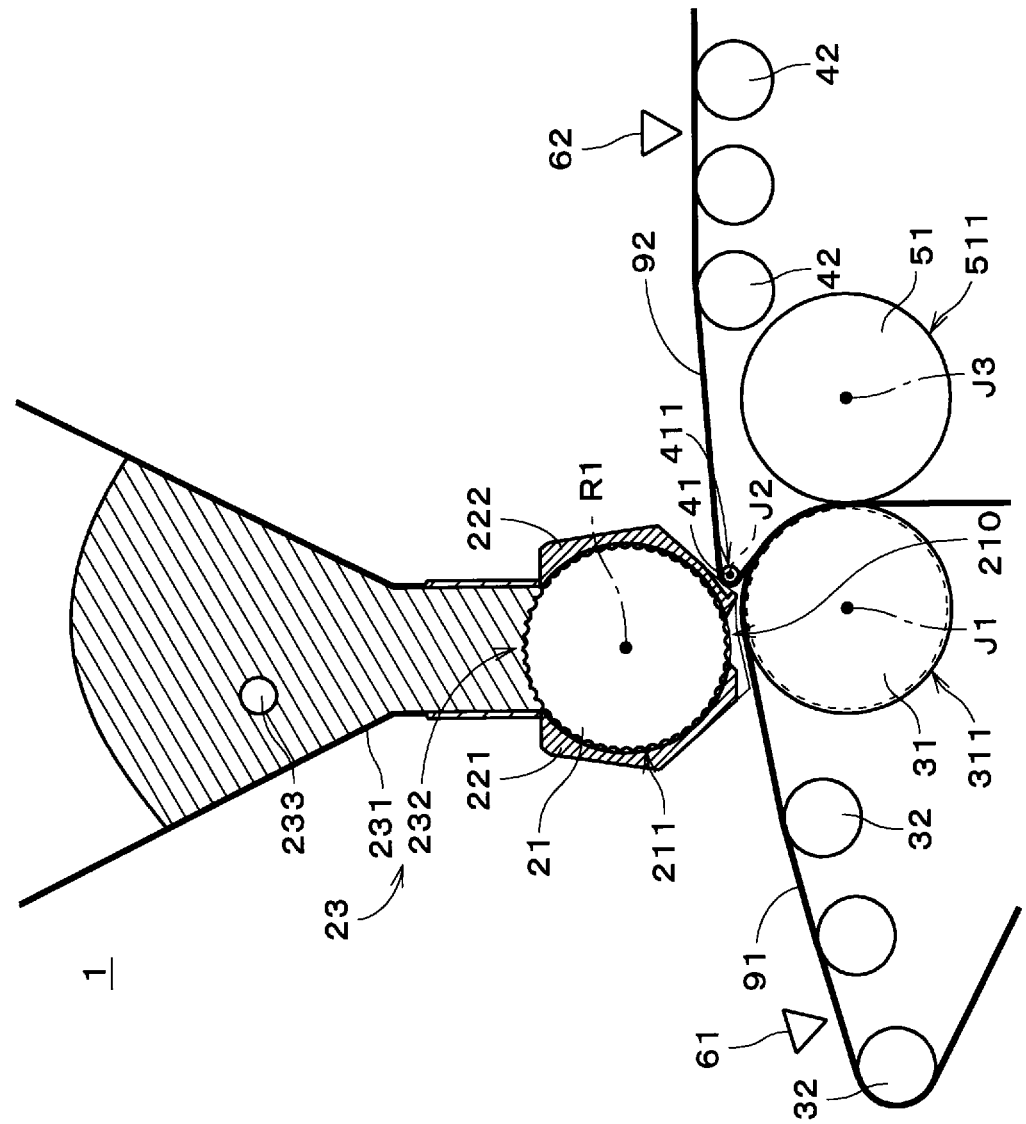
FIG. 1 illustrates a configuration of an absorbent sheet manufacturing apparatus according to a first embodiment.

FIG. 1 illustrates a configuration of an absorbent sheet manufacturing apparatus 1 according to a first embodiment of the present invention. The absorbent sheet manufacturing apparatus 1 is one absorbent-article sheet member manufacturing apparatus, and manufactures absorbent sheets by sandwiching particles of an absorbent material between sheet members of a nonwoven fabric or the like. The absorbent sheets are absorbent-article sheet members for use in absorbent articles such as disposable diapers or absorbent pads for light incontinence.

As the particles of an absorbent material, the absorbent sheet manufacturing apparatus 1 uses, for example, particles of crosslinked materials of partially neutralized polyacrylic acids, hydrolysates of starch-acrylic acid graft polymers, saponified materials of vinyl acetate-acrylate copolymers, hydrolysates of acrylonitrile copolymers or acrylamide copolymers or crosslinked materials of these hydrolysates, crosslinked materials of cationic monomers, or crosslinked products of polyamino acid.

The absorbent sheet manufacturing apparatus 1 includes a supply cylinder 21 that is a generally cylindrical member centered on a rotational axis (hereinafter, referred to as a "cylinder rotation axis") R1 pointing in a horizontal direction, a first sheet conveying roller 31 having a generally columnar shape centered on a first central axis J1 pointing in a direction (hereinafter referred to as an "axial direction") parallel to the cylinder rotation axis R1, a second sheet conveying roller 41 having a generally columnar shape centered on a second central axis J2 pointing in the axial direction, and a bonding roller 51 having a generally columnar shape centered on a third central axis J3 pointing in the axial direction. For ease of understanding of the drawing, the cross-sections of the supply cylinder 21 and each roller are not diagonally hatched in FIG. 1 (the same applies to the other drawings).

The supply cylinder 21, the first sheet conveying roller 31, and the bonding roller 51 have approximately the same diameter. The diameter of the second sheet conveying roller 41 is smaller than those of the supply cylinder 21, the first sheet conveying roller 31, and the bonding roller 51. The supply cylinder 21 has a cylinder outer surface 211 that is a generally cylindrical surface centered on the cylinder rotation axis R1. The first sheet conveying roller 31 has a first roller outer surface 311 that is a generally cylindrical surface centered on the first central axis J1. The second sheet conveying roller 41 has a second roller outer surface 411 that is a generally cylindrical surface centered on the second central axis J2. The bonding roller 51 has a bonding roller outer surface 511 that is a generally cylindrical surface centered on the third central axis J3.

The first sheet conveying roller 31 is disposed below the supply cylinder 21, and the lowermost part of the supply cylinder 21 and the uppermost part of the first sheet conveying roller 31 are in close proximity to each other. The first central axis J1 of the first sheet conveying roller 31 is located to the right of the cylinder rotation axis R1 of the supply cylinder 21 in FIG. 1. The second sheet conveying roller 41 is disposed to the right of the lowermost part of the supply cylinder 21 and the uppermost part of the first sheet conveying roller 31 in FIG. 1 and in close proximity to the supply cylinder 21 and the first sheet conveying roller 31. More specifically, the second central axis J2 and the second sheet conveying roller 41 as a whole are located to the right of the lowermost part of the supply cylinder 21 and the uppermost part of the first sheet conveying roller 31 in FIG. 1 and between the cylinder outer surface 211 and the first roller outer surface 311 that face each other in the up-down direction. The bonding roller 51 is disposed adjacent to the right side of the first sheet conveying roller 31 in FIG. 1.

The absorbent sheet manufacturing apparatus 1 further includes a plurality of auxiliary rollers 32 and 42, each having a generally columnar shape centered on a central axis pointing in the axial direction, and first and second application parts 61 and 62 for applying an adhesive (in the present embodiment, a hot-melt adhesive). The plurality of auxiliary rollers 32 and the first application part 61 are located to the left of the supply cylinder 21 and the first sheet conveying roller 31 in FIG. 1. The plurality of auxiliary rollers 42 and the second application part 62 are located to the right of the bonding roller 51 in FIG. 1.

The supply cylinder 21 rotates counterclockwise in FIG. 1, which is a predetermined rotation direction, about the cylinder rotation axis R1. The supply cylinder 21 supplies, in the vicinity of the lowermost part, particles of an absorbent material (e.g., particles of a highly absorbent resin such as a super absorbent polymer (SAP); hereinafter, simply referred to as "particles") onto a first sheet member 91 that is a continuous sheet made of a nonwoven fabric or the like. The first sheet conveying roller 31 rotates about the first central axis J1 in the opposite direction to the rotation direction of the supply cylinder 21 (i.e., rotates clockwise in FIG. 1) to convey the first sheet member 91 along the first roller outer surface 311 to the vicinity of the lowermost part of the supply cylinder 21.

The second sheet conveying roller 41 rotates about the second central axis J2 in the same direction as the rotation direction of the supply cylinder 21 (i.e., rotates counterclockwise in FIG. 1) in synchronization with the rotation of the first sheet conveying roller 31. The second sheet conveying roller 41 conveys a second sheet member 92 that is a continuous sheet made of a nonwoven fabric or the like along the second roller outer surface 411 to the vicinity of the lowermost part of the supply cylinder 21. As described above, the second sheet conveying roller 41 is disposed to the right of the lowermost part of the supply cylinder 21 in FIG. 1, i.e., forward of the lowermost part of the supply cylinder 21 in the rotation direction of the supply cylinder 21. The second sheet conveying roller 41 is also disposed forward of the uppermost part of the first sheet conveying roller 31 in the rotation direction of the first sheet conveying roller 31. The second sheet member 92 conveyed by the second sheet conveying roller 41 to the vicinity of the lowermost part of the supply cylinder 21 (i.e., the vicinity of the uppermost part of the first sheet conveying roller 31) is layered on the first sheet member 91 that has passed the uppermost part of the first sheet conveying roller 31.

The bonding roller 51 rotates counterclockwise in FIG. 1 about the third central axis J3 in synchronization with the rotation of the first sheet conveying roller 31. Like the bonding roller 51, each auxiliary roller 42 also rotates counterclockwise in FIG. 1. Each auxiliary roller 32 rotates clockwise in FIG. 1, similarly to the first sheet conveying roller 31. The first application part 61 is disposed above the plurality of auxiliary rollers 32 and applies an adhesive onto the first sheet member 91. The second application part 62 is disposed above the plurality of auxiliary rollers 42 and applies an adhesive onto the second sheet member 92.

The second sheet member 92 that has passed the second sheet conveying roller 41 is layered on the first sheet member 91. The first sheet member 91 and the second sheet member 92 are then sandwiched between the first sheet conveying roller 31 and the bonding roller 51 and thereby bonded to each other. The first sheet conveying roller 31 and the bonding roller 51 constitute a sheet bonding part for bonding the first sheet member 91 and the second sheet member 92 to each other.

A particle filling part 23 is provided above the supply cylinder 21. The particle filling part 23 includes a particle tank 231 that is disposed above the supply cylinder 21 and is for housing highly absorbent resin particles, and a level sensor 233 provided in the particle tank 231. When the level sensor 233 has detected that the amount of particles in the particle tank 231 is less than or equal to a certain amount, the particle tank 231 is replenished with particles. The particle tank 231 extends approximately parallel to the direction of gravity, and a particle filling opening 232 that faces the cylinder outer surface 211 of the supply cylinder 21 is formed at the lower end of the particle tank 231. The particle filling opening 232 faces an area of the supply cylinder 21 that includes the uppermost part thereof.

A first cover part 221 and a second cover part 222 are provided around the supply cylinder 21. The first cover part 221 extends from the particle filling opening 232 to the lower part of the supply cylinder 21 in the rotation direction of the supply cylinder 21 (i.e., counterclockwise in FIG. 1). The first cover part 221 is a half cover part for covering part of the cylinder outer surface 211 on the left side of the supply cylinder 21. The second cover part 222 extends from the particle filling opening 232 to the lower part of the supply cylinder 21 in the opposite direction (i.e., clockwise in FIG. 1) to the rotation direction of the supply cylinder 21. The second cover part 222 is another half cover part for covering another part of the cylinder outer surface 211 on the right side of the supply cylinder 21.

Of the cylinder outer surface 211 of the supply cylinder 21, a region between the lower end of the first cover part 221 and the lower end of the second cover part 222, i.e., a region of the cylinder outer surface 211 that is exposed from the first cover part 221 and the second cover part 222 at the lower part of the supply cylinder 21, is a particle supply region 210 to which particles are supplied as will be described later. The first cover part 221 extends clockwise from the particle supply region 210, and the second cover part 222 extends counterclockwise from the particle supply region 210.

Figure 2:
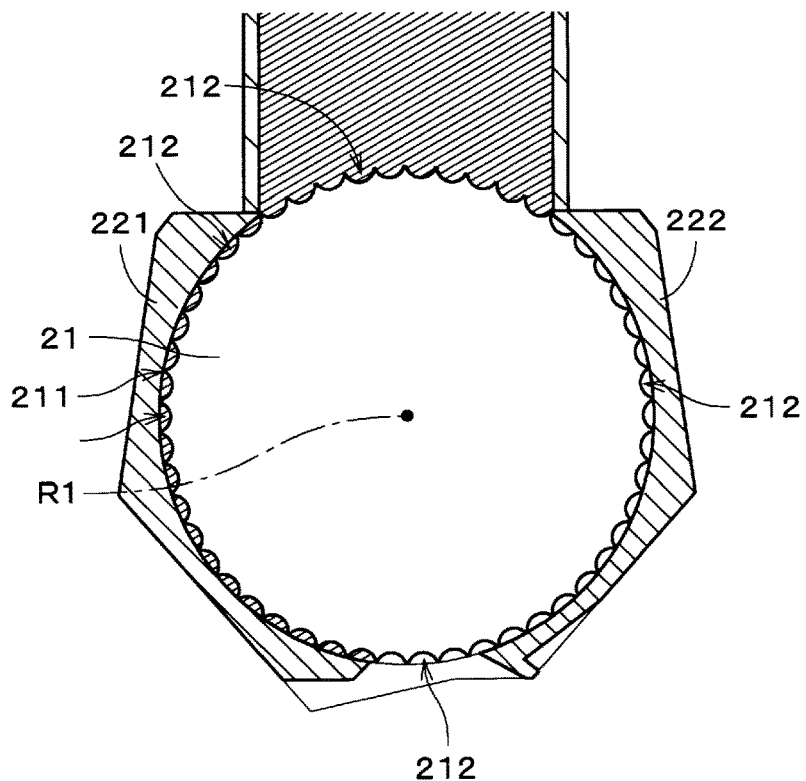
FIG. 2 is a cross-sectional view of a supply cylinder and other constituent elements.
Figure 3:
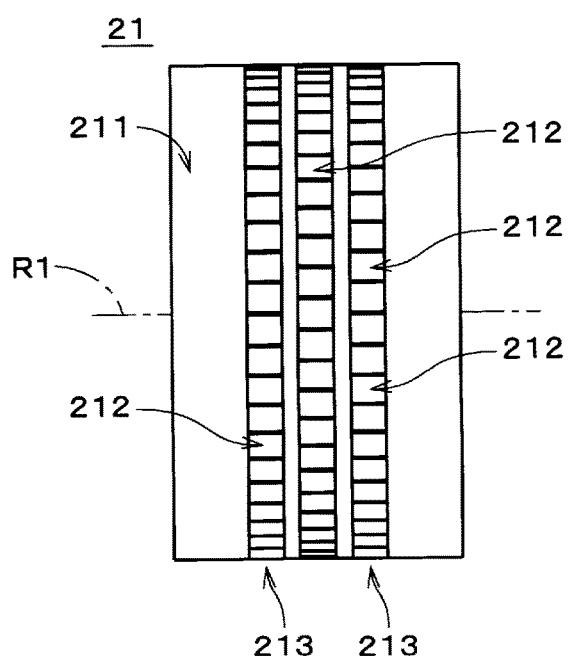
FIG. 3 is a front view of the supply cylinder.

FIG. 2 is an enlarged cross-sectional view of a configuration of the supply cylinder 21 and the vicinity of the supply cylinder 21. FIG. 2 illustrates a cross-section perpendicular to the cylinder rotation axis R1 and also illustrates an area located behind the cross-section (the same applies to FIGS. 5, 6, 10, 13, and 15). FIG. 3 illustrates the cylinder outer surface 211 of the supply cylinder 21 as viewed in a direction perpendicular to the cylinder rotation axis R1. In FIG. 2, the particles are finely diagonally hatched. Illustration of the first cover part 221 and the second cover part 222 is omitted in FIG. 3.

As illustrated in FIGS. 2 and 3, the cylinder outer surface 211 of the supply cylinder 21 has a plurality of supply holes (hereinafter, the supply holes are referred to as "recessed supply portions 212") arrayed in close proximity to each other and fully circumferentially about the cylinder rotation axis R1 at a plurality of positions in the axial direction. When a group of recessed supply portions that are arrayed circumferentially at the same position in the axial direction as illustrated in FIG. 3 is referred to as a "recessed supply portion row 213," the above-described plurality of recessed supply portions 212 include a plurality of recessed supply portion rows 213 (i.e., supply hole rows). The plurality of recessed supply portions 212 include, for example, three recessed supply portion rows 213. Each recessed supply portion 212 has, for example, a generally rectangular shape as viewed in a direction perpendicular to the cylinder rotation axis R1. The bottom surface of each recessed supply portion 212 in a cross-section perpendicular to the cylinder rotation axis R1 has, for example, an approximately arc-like shape as illustrated in FIG. 2. The recessed supply portions 212 may be of various shapes, and for example, each recessed supply portion 212 may have a generally rectangular shape in a cross-section perpendicular to the cylinder rotation axis R1. The number of recessed supply portion rows 213 formed in the cylinder outer surface 211 may be one, two, or four or more.

As illustrated in FIG. 2, the areas of the supply cylinder 21 that are covered by the first cover part 221 and the second cover part 222, excluding the recessed supply portions 212 of the cylinder outer surface 211, are in extremely close proximity to or substantially in contact with the inner surface of the first cover part 221 and the inner surface of the second cover part 222.

Figure 4:
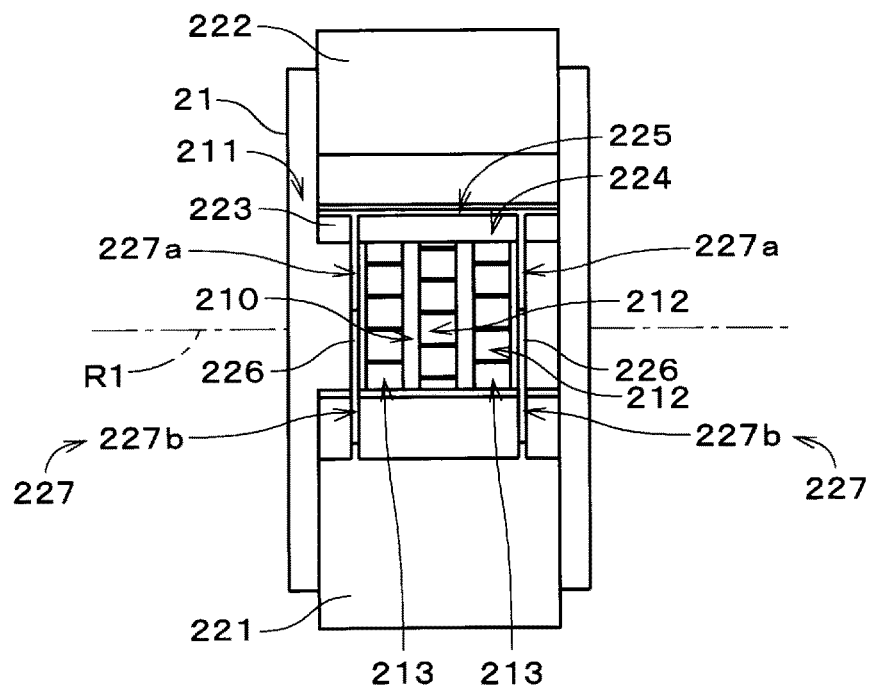
FIG. 4 is a bottom view of the supply cylinder and other constituent elements.
Figure 5:
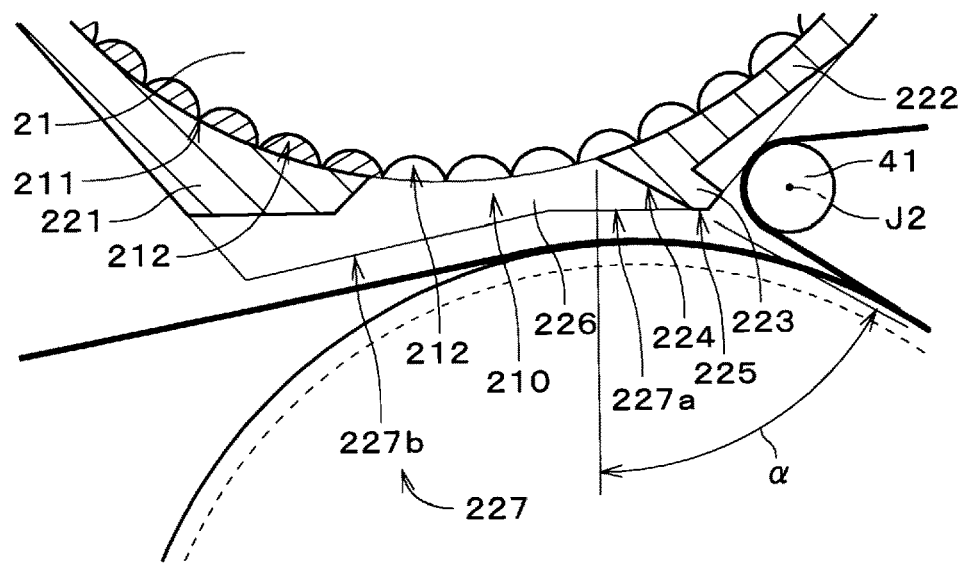
FIG. 5 is a cross-sectional view of the supply cylinder and other constituent elements.

FIG. 4 is a bottom view of the lower parts of the supply cylinder 21, the first cover part 221, and the second cover part 222, i.e., the particle supply region 210 and the area in the vicinity of the particle supply region 210. FIG. 5 is an enlarged cross-sectional view of an area in the vicinity of the particle supply region 210. As illustrated in FIGS. 4 and 5, the lower end of the second cover part 222 has a front wall part 223 that protrudes in a direction away from the cylinder outer surface 211 (i.e., outward of the radial direction of the supply cylinder 21). The front wall part 223 is a plate-like member extending in the axial direction and, similarly to the first cover part 221 and the second cover part 222, is provided across the entire width in the axial direction of the region where the plurality of recessed supply portion rows 213 are arranged. The front wall part 223, the first cover part 221, and the second cover part 222 extend to the outside of the region where the plurality of recessed supply portion rows 213 are arranged, on both sides of the region in the axial direction.

The front wall part 223 has a generally planar particle collision surface 224 on the left side in FIG. 5 (i.e., back side in the rotation direction of the supply cylinder 21) that extends parallel to the axial direction. The particle collision surface 224 extend downward from the cylinder outer surface 211 in between the lowermost part of the supply cylinder 21 and the second sheet conveying roller 41. The upper end edge of the particle collision surface 224 faces the cylinder outer surface 211 with a slight space in between. The lower end edge of the particle collision surface 224 is located below or at the same position as the second central axis J2 of the second sheet conveying roller 41 in the up-down direction. In FIG. 5, the lower end edge of the particle collision surface 224 is located below the second central axis J2 of the second sheet conveying roller 41 in the up-down direction. A lower end surface 225 of the front wall part 223 extends approximately horizontally from the lower end edge of the particle collision surface 224 to the right in FIG. 5.

The particle collision surface 224 is inclined to the right in FIG. 5 with respect to a vertical plane including the upper end edge of the particle collision surface 224. In other words, the particle collision surface 224 is an inclined surface that is inclined forward in the rotation direction of the supply cylinder 21 with respect to a vertically downward direction. An angle α formed by the above vertical plane and the particle collision surface 224 is preferably greater than or equal to 30 degrees and less than or equal to 90 degrees. In FIG. 5, the angle α is approximately 65 degrees. The particle collision surface 224 is also inclined to the right in FIG. 5 (i.e., forward in the rotation direction of the supply cylinder 21) with respect to a plane that includes the cylinder rotation axis R1 (see FIG. 2) of the supply cylinder 21 and the upper end edge of the particle collision surface 224.

As illustrated in FIGS. 4 and 5, a pair of side wall parts 226 is provided below the supply cylinder 21. The side wall parts 226 of the pair are disposed on both sides in the axial direction of the plurality of recessed supply portions 212 (i.e., a group of supply holes) that are exposed from the first cover part 221 and the second cover part 222 in the particle supply region 210. In other words, the side wall parts 226 of the pair are disposed on both sides in the axial direction of the plurality of recessed supply portions 212 of the cylinder outer surface 211 that are exposed between the lower end of the first cover part 221 and the particle collision surface 224.

Each side wall part 226 of the pair is a plate-like member that is approximately perpendicular to the cylinder rotation axis R1 and extends downward from the cylinder outer surface 211. Each side wall part 226 of the pair is provided in close proximity to the cylinder outer surface 211 and continuously from the lower end of the first cover part 221 to the particle collision surface 224. The pair of side wall parts 226 connects the lower end of the first cover part 221 and the front wall part 223 located at the lower end of the second cover part 222. Thus, the first cover part 221, the front wall part 223 having the particle collision surface 224, the second cover part 222, and the pair of side wall parts 226 are included in an integral member that surrounds the supply cylinder 21.

A lower end surface 227 of each side wall part 226 of the pair includes a horizontal portion 227a and an inclined portion 227b. The horizontal portion 227a extends approximately horizontally forward in the rotation direction of the supply cylinder 21 from below the vicinity of the lowermost part of the supply cylinder 21, and is contiguous with the lower end surface 225 of the front wall part 223. The inclined portion 227b is contiguous with the horizontal portion 227a below the vicinity of the lowermost part of the supply cylinder 21 and extends downward as it extends backward in the rotation direction of the supply cylinder 21. In other words, the inclined portion 227b extends downward as it extends from the particle collision surface 224 toward the first cover part 221.

In the absorbent sheet manufacturing apparatus 1 illustrated in FIG. 1, the supply cylinder 21 rotates at a high speed about the cylinder rotation axis R1, and the plurality of recessed supply portions 212 (see FIG. 2) passing under the particle tank 231 of the particle filling part 23 are successively replenished with particles through the particle filling opening 232 under the force of gravity.

In the absorbent sheet manufacturing apparatus 1, the outer sides of the recessed supply portions 212 filled with particles are covered by the first cover part 221 (i.e., the recessed supply portions 212 are covered from the cylinder outer surface 211 side) until when the recessed supply portions 212 reach the particle supply region 210 provided at the lower part of the supply cylinder 21. Then, when each recessed supply portion 212 passes over the edge of the first cover part 221 at the lower part of the supply cylinder 21, i.e., the front edge of the first cover part 221 in the rotation direction of the supply cylinder 21, and passes through the particle supply region 210, particles in the recessed supply portion 212 are emitted to the outside of the supply cylinder 21. The particles from the recessed supply portions 212 are emitted forward in the rotation direction of the supply cylinder 21 approximately along a tangential direction to the cylinder outer surface 211 at positions away from the supply cylinder 21.

Figure 6:
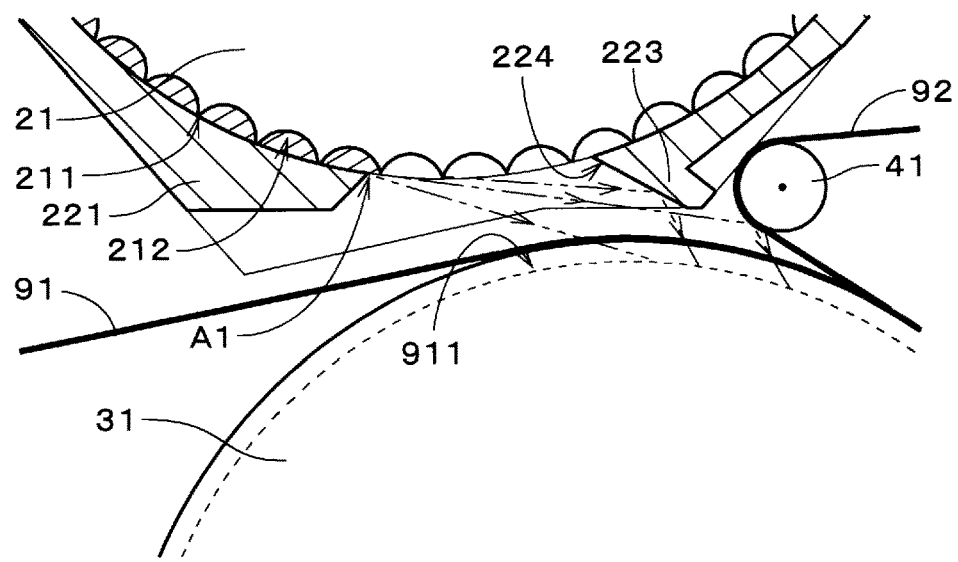
FIG. 6 is a cross-sectional view of the supply cylinder and other constituent elements.

FIG. 6 illustrates how particles are emitted from the supply cylinder 21. In FIG. 6, travel paths of some of the particles emitted from the supply cylinder 21 are indicated by dashed double-dotted lines and arrows (the same applies to FIG. 15). The emission of particles from the supply cylinder 21 starts at the instant when the recessed supply portions 212 have passed over the front edge of the first cover part 221. In the following description, the position of this front edge is referred to as an "emission start position A1." The emission start position A1 is located backward (upstream) of the lowermost part of the supply cylinder 21 in the rotation direction of the supply cylinder 21 and in the vicinity of the lowermost part of the supply cylinder 21. As described previously, the supply cylinder 21 rotates at a high speed and emits particles from each of the plurality of recessed supply portions 212 approximately along a tangent to the cylinder outer surface 211. Particles that are emitted at approximately the emission start position A1 are supplied directly to the first sheet member 91 on the first sheet conveying roller 31 as illustrated in FIG. 6.

Figure 7:
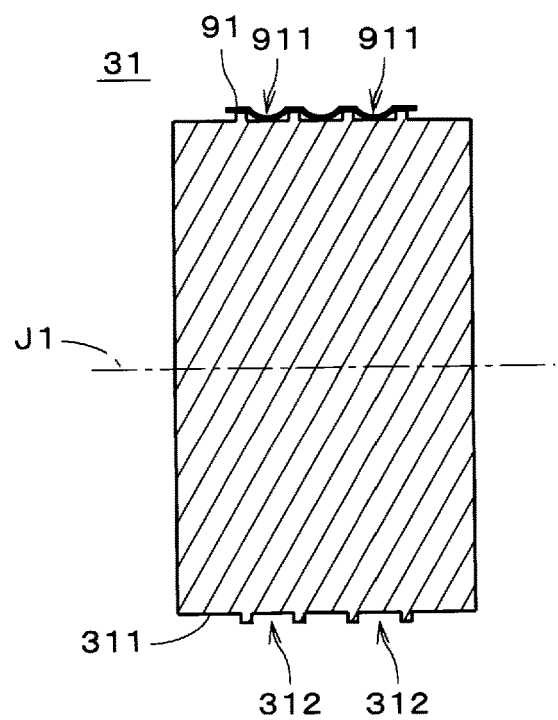
FIG. 7 is a cross-sectional view of a first sheet conveying roller.

FIG. 7 is a cross-sectional view of the first sheet conveying roller 31. FIG. 7 illustrates a cross-section taken along a plane that includes the first central axis J1 of the first sheet conveying roller 31. The first roller outer surface 311 has annular grooves 312 formed at a plurality of positions in the axial direction and extending circumferentially about the first central axis J1. The number of annular grooves 312 is equal to the number of recessed supply portion rows 213 (in the present embodiment, three) of the supply cylinder 21 illustrated in FIG. 3. The plurality of annular grooves 312 illustrated in FIG. 7 are arranged at the same positions as the positions of the plurality of recessed supply portion rows 213 in the axial direction.

The first sheet conveying roller 31 is configured such that the first roller outer surface 311 has a relatively large diameter and the first sheet member 91 is pulled under a constant tension along the first roller outer surface 311. Thus, areas 911 of the first sheet member 91 that correspond to the annular grooves 312 have a shape recessed toward the bottom of the annular grooves 312. In other words, the first sheet member 91 has groove portions 911 corresponding to the annular grooves 312. Since, as described above, the annular grooves 312 of the first sheet conveying roller 31 are located at the same positions as the positions of the plurality of recessed supply portion rows 213 in the axial direction, particles emitted from each recessed supply portion 212 toward the first sheet member 91, as illustrated in FIG. 6, are directed toward the groove portions 911 and housed in the groove portions 911. At this time, even if particles bounce around inside the groove portions 911, the side walls of the groove portions 911 suppress scattering of the particles to the outside of the groove portions 911.

Particles that are emitted from the recessed supply portions 212 at a slight delay after having passed the emission start position A1 pass between the first sheet member 91 on the first sheet conveying roller 31 and the lower end of the particle collision surface 224 and collide directly with the second sheet member 92 on the second sheet conveying roller 41. The particles then bounce back off the second sheet member 92 and are supplied to the groove portions 911 of the first sheet member 91 that is being conveyed under the second sheet member 92. Particles that are emitted at a further delay from the recessed supply portions 212 collide directly with the particle collision surface 224 of the front wall part 223, bounce back off the particle collision surface 224, and are supplied to the groove portions 911 of the first sheet member 91 that is being conveyed under the particle collision surface 224.

In the absorbent sheet manufacturing apparatus 1, the first sheet member 91 is guided on the plurality of auxiliary rollers 32 illustrated in FIG. 1 to the first sheet conveying roller 31. At this time, the first application part 61 applies an adhesive to a plurality of strip regions (or linear regions) of the first sheet member 91 that are to be layered on the plurality of annular grooves 312 (see FIG. 7). These plurality of strip regions (hereinafter, referred to as "adhesive application regions") are located at the same positions as the positions of the plurality of recessed supply portion rows 213 (see FIG. 3) of the supply cylinder 21 and the plurality of annular grooves 312 in the axial direction. Thus, the first sheet member 91 has the aforementioned adhesive application regions located at the groove portions 911 illustrated in FIGS. 6 and 7. This allows particles supplied to the groove portions 911 of the first sheet member 91 to be easily caught in the groove portions 911.

As described above, in the absorbent sheet manufacturing apparatus 1, particles are emitted from the plurality of recessed supply portions 212 by the rotation of the supply cylinder 21 and supplied to the first sheet member 91 either directly or indirectly via the second sheet member 92 or the particle collision surface 224. Each recessed supply portion 212 that has supplied particles to the first sheet member 91 passes through the particle supply region 210 illustrated in FIG. 1 and, with its outer side covered by the second cover part 222, travels toward the upper part of the supply cylinder 21 to the particle filling opening 232 of the particle filling part 23.

On the other hand, the second sheet member 92 is guided on the plurality of auxiliary rollers 42 to the second sheet conveying roller 41. At this time, the second application part 62 applies an adhesive in strips to the same positions of the second sheet member 92 as the positions of the plurality of groove portions 911 of the first sheet member 91 in the axial direction. The sheet member 92, after having passed the second sheet conveying roller 41, is layered on the first sheet member 91 in which particles have been supplied to each groove portion 911.

The first sheet member 91 and the second sheet member 92 are sandwiched between the first roller outer surface 311 of the first sheet conveying roller 31 and the bonding roller outer surface 511 of the bonding roller 51. Both (or only one) of the first sheet conveying roller 31 and the bonding roller 51 are provided with a heater, and regions of the first sheet member 91 and the second sheet member 92 that are in contact with raised portions of the first roller outer surface 311 of the first sheet conveying roller 31 on both sides of the annular grooves 312 (see FIG. 6) are sealed by heat. Accordingly, the first sheet member 91 and the second sheet member 92 are bonded to each other.

Figure 8:
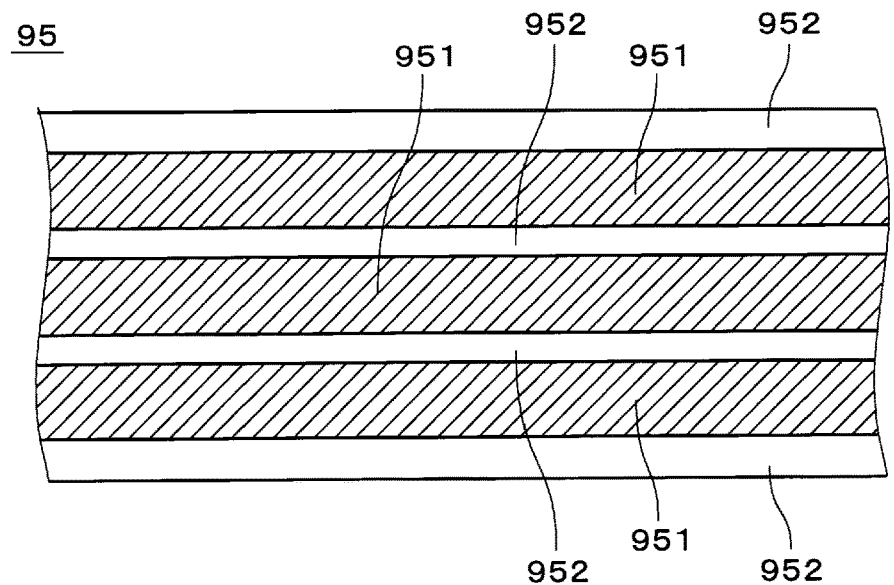
FIG. 8 is a plane view of an absorbent sheet.

This consequently produces an absorbent sheet 95 as illustrated in FIG. 8 in which a plurality of strip-like (or linear) particle existence regions 951 where highly absorbent resin particles are distributed and a plurality of strip-like (or linear) particle-free regions 952 where the first sheet member 91 and the second sheet member 92 are bonded together and substantially no particles are present are alternately arranged in the width direction. In other words, the absorbent sheet 95 has a plurality of particle existence regions 951 formed in strips. The particle existence regions 951 are diagonally hatched in FIG. 8.

As described above, the absorbent sheet manufacturing apparatus 1 includes the particle collision surface 224 that extends from the cylinder outer surface 211 in between the lowermost part of the supply cylinder 21 and the second sheet conveying roller 41. Some of the particles emitted forward in the rotation direction of the supply cylinder 21 from the recessed supply portions 212 that have passed the first cover part 221 collide with the particle collision surface 224, and the colliding particles are guided by the particle collision surface 224 to the first sheet member 91.

This reduces the number of particles that collide directly with the second sheet member 92 on the second sheet conveying roller 41 among the particles emitted from the supply cylinder 21. In other words, direct collision of particles emitted from the supply cylinder 21 with the second sheet member 92 on the second sheet conveying roller 41 can be suppressed. It is thus possible to suppress scattering of particles that have collided with the second sheet member 92 around the first sheet member 91 and the second sheet member 92. This results in efficient supply of particles from the supply cylinder 21 to the first sheet member 91.

As described above, in the absorbent sheet manufacturing apparatus 1, the lower end of the particle collision surface 224 is located below or at the same position as the second central axis J2 of the second sheet conveying roller 41 in the up-down direction. Thus, particles emitted from the recessed supply portions 212 that have passed the first cover part 221 toward the space between the lower end of the particle collision surface 224 and the first sheet member 91 on the first sheet conveying roller 31 collide directly with the second sheet member 92 on the second sheet conveying roller 41 at positions below the second central axis J2 of the second sheet conveying roller 41. Thus, particles emitted from the supply cylinder 21 are prevented from colliding with the second sheet member 92 on the second sheet conveying roller 41 at positions above the second central axis J2. This further suppresses scattering of particles that have collided with the second sheet member 92 in the surroundings.

The particle collision surface 224 is, as described above, an inclined surface that is inclined forward in the rotation direction of the supply cylinder 21 with respect to a vertically downward direction. This reduces the impact when particles collide with the particle collision surface 224. Consequently, particles that have collided with the particle collision surface 224 can be guided onto the first sheet member 91 while suppressing scattering of the particles in the surroundings. The particle collision surface 224 is also inclined forward in the rotation direction of the supply cylinder 21 with respect to a plane that includes the cylinder rotation axis R1 of the supply cylinder 21 and the upper end edge of the particle collision surface 224. This further suppresses scattering of particles that have collided with the particle collision surface 224 in the surroundings.

In the absorbent sheet manufacturing apparatus 1, the side wall parts 226 of the pair are disposed on both sides in the axial direction of the group of the recessed supply portions 212 of the cylinder outer surface 211 that are exposed between the lower end of the first cover part 221 and the particle collision surface 224. Each side wall part 226 is provided in close proximity to the cylinder outer surface 211 and continuously from the lower end of the first cover part 221 to the particle collision surface 224, and extends downward from the cylinder outer surface 211. This reduces the possibility that particles emitted sideways from the recessed supply portions 212 in the particle supply region 210 or particles that have collided with the first roller outer surface 311 (in particular, raised portions on both sides of the annular grooves 312) of the first sheet conveying roller 31 and then bounced sideways move to the outside of the side wall parts 226. In other words, particles can be guided onto the first sheet member 91 while suppressing wide sideways scattering of the particles.

Incidentally, when the supply cylinder 21 rotates at a relatively low speed, particles in the recessed supply portions 212 are emitted in a direction away from the cylinder outer surface 211, rather than in a tangential direction to the cylinder outer surface 211, in the vicinity of the emission start position A1. Then, the particles collide with the first sheet member 91 at positions relatively far away from the uppermost portion of the first sheet conveying roller 31 and backward in the radial direction. In the absorbent sheet manufacturing apparatus 1, as described above, the lower end of each side wall part 226 of the pair includes the inclined portion 227b that is inclined downward as it extends from the particle collision surface 224 toward the first cover part 221, and the side wall parts 226 are in close proximity to the first roller outer surface 311 downstream of the uppermost portion of the first sheet conveying roller 31 in the radial direction. Thus, sideways scattering of particles can be suppressed even if the supply cylinder 21 rotates at a relatively low speed.

As described above, the first cover part 221, the particle collision surface 224, and the pair of side wall parts 226 are included in an integral member. This eliminates the need, when manufacturing the absorbent sheet manufacturing apparatus 1, to assemble a plurality of components that correspond respectively to the first cover part 221, the particle collision surface 224, and the pair of side wall parts 226 and accordingly facilitates the manufacture of the absorbent sheet manufacturing apparatus 1.

Figure 9:
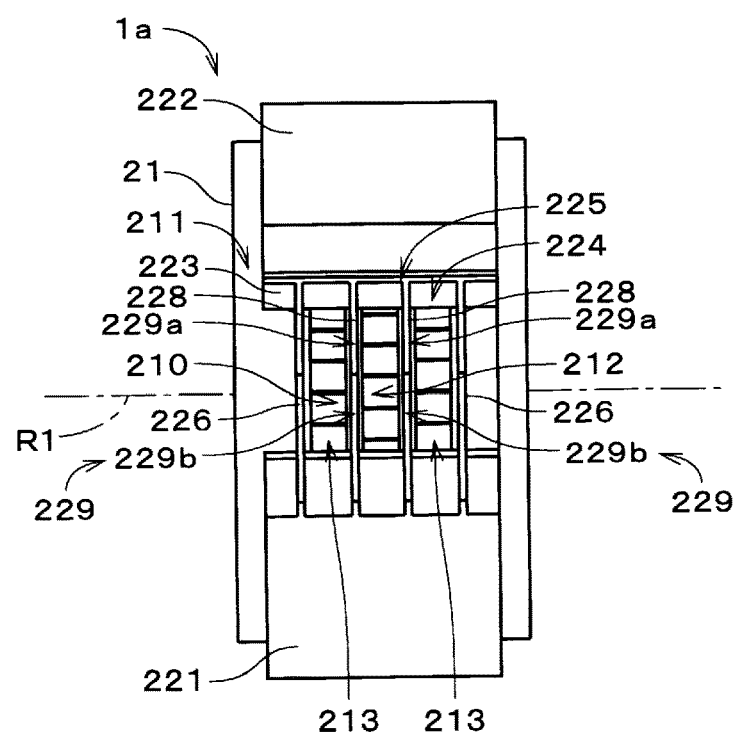
FIG. 9 is a bottom view of a supply cylinder and other constituent elements of an absorbent sheet manufacturing apparatus according to a second embodiment.

FIG. 9 is a bottom view of a particle supply region 210 and areas in the vicinity of the particle supply region in an absorbent sheet manufacturing apparatus 1a according to a second embodiment of the present invention. In the absorbent sheet manufacturing apparatus 1a, partition parts 228 are provided below the supply cylinder 21. The other constituent elements are substantially the same as those of the absorbent sheet manufacturing apparatus 1 illustrated in FIG. 1, and constituent elements that correspond to those in FIG. 1 are given the same reference numerals.

As illustrated in FIG. 9, two partition parts 228 are provided between the pair of side wall parts 226 in the axial direction. Each partition part 228 is a plate-like member that is approximately perpendicular to the cylinder rotation axis R1 and extends downward from the cylinder outer surface 211. Each partition part 228 faces an area of the cylinder outer surface 211 between a plurality of recessed supply portion rows 213 in the particle supply region 210. Each partition part 228 is provided in close proximity to the cylinder outer surface 211 and continuously from the lower end of the first cover part 221 to the particle collision surface 224. Each partition part 228 is included in the aforementioned integral member that includes the first cover part 221, the front wall part 223 having the particle collision surface 224, the second cover part 222, and the pair of side wall parts 226.

Figure 10:
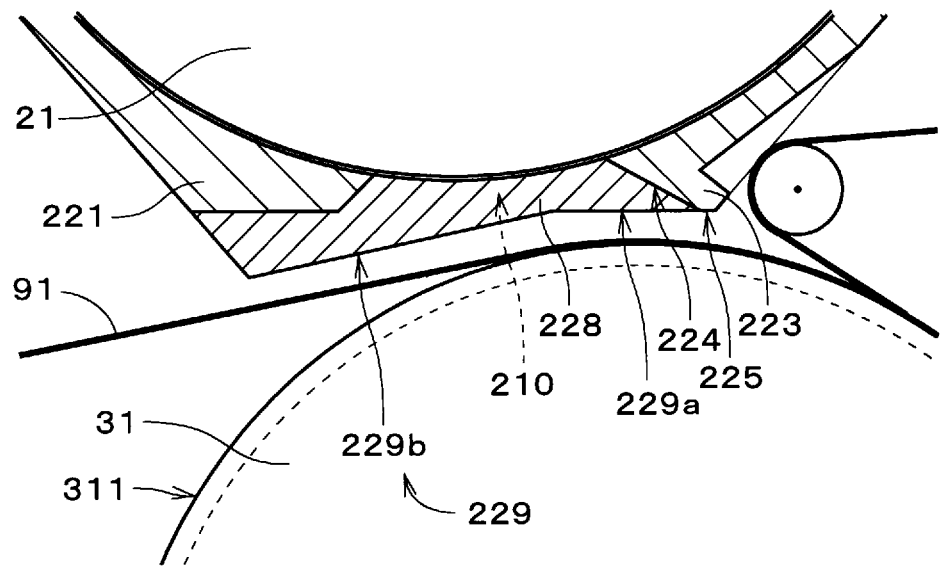
FIG. 10 is a cross-sectional view of the supply cylinder and other constituent elements.

FIG. 10 is an enlarged cross-sectional view of an area in the vicinity of the particle supply region 210. FIG. 10 illustrates a cross-section taken along one of the partition parts 228. As illustrated in FIGS. 9 and 10, a lower end surface 229 of each partition part 228 includes a horizontal portion 229a and an inclined portion 229b. The horizontal portion 229a extends approximately horizontally forward in the rotation direction of the supply cylinder 21 from below the vicinity of the lowermost part of the supply cylinder 21 and is contiguous with the lower end surface 225 of the front wall part 223. The inclined portion 229b is contiguous with the horizontal portion 229a below the vicinity of the lowermost part of the supply cylinder 21 and extends downward as it extends backward in the rotation direction of the supply cylinder 21. In other words, the inclined portion 229b extends downward as it extends from the particle collision surface 224 toward the first cover part 221.

The absorbent sheet manufacturing apparatus 1a provided with the partition parts 228 can suppress sideways scattering of particles emitted from the recessed supply portions 212 included in each of the recessed supply portion rows 213. More specifically, the apparatus reduces the possibility that particles emitted from each recessed supply portion row 213 will be supplied under other recessed supply portion rows 213 or under the area between adjacent two recessed supply portion rows 213 on the first sheet member 91. Accordingly, the absorbent sheet 95 as illustrated in FIG. 8 in which the plurality of particle existence regions 951 are formed in distinct strips can be readily manufactured.

In addition, in the absorbent sheet manufacturing apparatus 1a, the lower end of each partition part 228 includes the inclined portion 229b that is inclined downward as it extends from the particle collision surface 224 toward the first cover part 221, and the partition parts 228 are in close proximity to the first roller outer surface 311 backward of the uppermost portion of the first sheet conveying roller 31 in the radial direction. Thus, sideways scattering of particles emitted from each recessed supply portion row 213 can be suppressed even if the supply cylinder 21 rotates at a relatively low speed.

Figure 11:
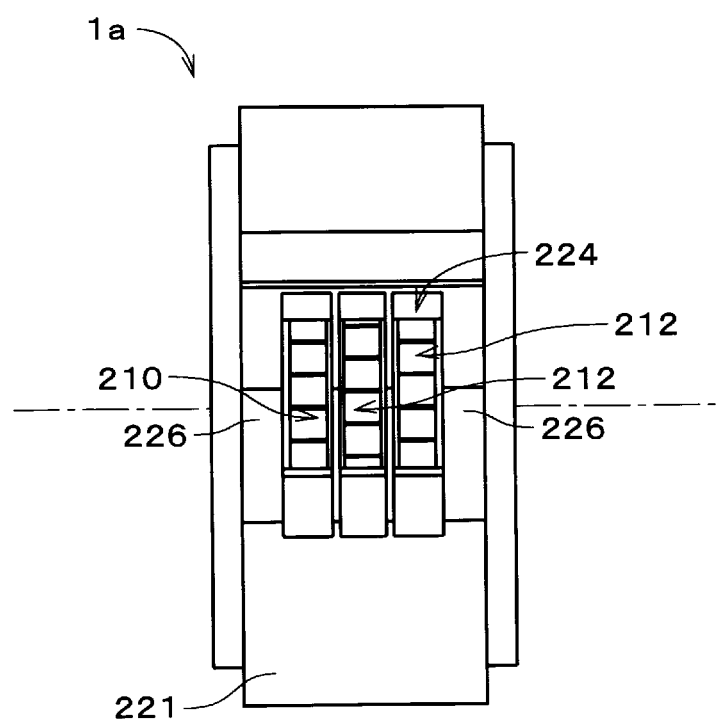
FIG. 11 is a bottom view of the supply cylinder and other constituent elements.

FIG. 11 illustrates another preferable example of the absorbent sheet manufacturing apparatus 1a. FIG. 11 is a bottom view of the particle supply region 210 and an area in the vicinity of the particle supply region. In the example illustrated in FIG. 11, each side wall part 226 has a greater thickness in the axial direction than in the example illustrated in FIG. 9, and both axial ends (i.e., ends on the side opposite to the recessed supply portions 212) of the pair of side wall parts 226 approximately coincide with both axial ends of the first cover part 221 and the particle collision surface 224. Both circumferential ends of each side wall part 226 are connected to the first cover part 221 and the particle collision surface 224 across the entire axial width. This improves the strength of the integral member that includes the first cover part 221, the particle collision surface 224, and the pair of side wall parts 226. From the viewpoint of improving the strength of the integral member, areas of the pair of side wall parts 226 and the plurality of partition parts 228 that overlap with the first cover part 221 in the up-down direction may be connected together in the axial direction.

Figure 12:
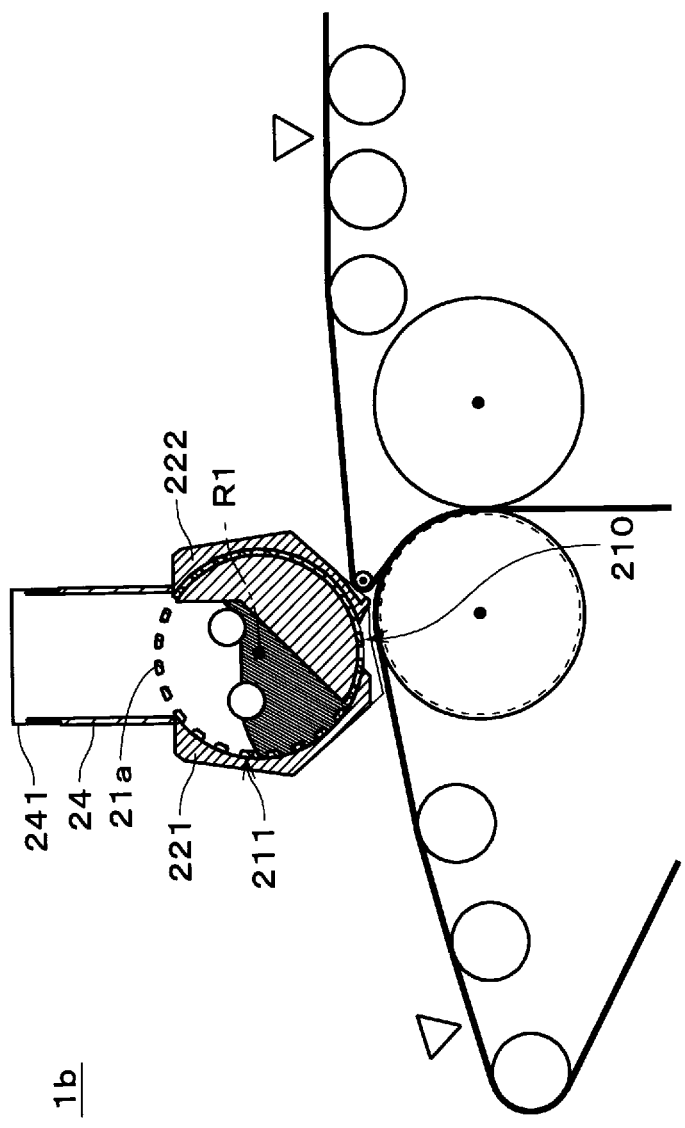
FIG. 12 illustrates a configuration of an absorbent sheet manufacturing apparatus according to a third embodiment.

FIG. 12 illustrates a configuration of an absorbent sheet manufacturing apparatus 1b according to a third embodiment of the present invention. The absorbent sheet manufacturing apparatus 1b includes, instead of the supply cylinder 21, a supply cylinder 21a that has a different structure from that of the supply cylinder 21 illustrated in FIG. 1. The other constituent elements are substantially the same as those of the absorbent sheet manufacturing apparatus 1 in FIG. 1, and constituent elements that correspond to those in FIG. 1 are given the same reference numerals.

The supply cylinder 21a illustrated in FIG. 12 is a generally cylindrical member centered on the cylinder rotation axis R1 pointing in the horizontal direction. Like the supply cylinder 21, the supply cylinder 21a rotates counterclockwise in FIG. 12 about the cylinder rotation axis R1. The supply cylinder 21a is rotated by driving a belt (not shown) that is wound circumferentially on the supply cylinder 21a.

A tubular exhaust part 24 is provided above the supply cylinder 21a, and an upper opening of the exhaust part 24 is covered by a bag-like filter 241 made of a nonwoven fabric or the like. As in the absorbent sheet manufacturing apparatus 1 illustrated in FIG. 1, the first cover part 221 and the second cover part 222 are provided around the supply cylinder 21a. The first cover part 221 extends from the particle supply region 210 at the lower part of the supply cylinder 21a to the exhaust part 24 in the opposite direction to the rotation direction of the supply cylinder 21a (i.e., clockwise in FIG. 12). The first cover part 221 is a half cover part that covers part of the cylinder outer surface 211 on the left side of the supply cylinder 21a. The second cover part 222 extends from the particle supply region 210 to the exhaust part 24 in the same direction as the rotation direction of the supply cylinder 21a. The second cover part 222 is another half cover part that covers another part of the cylinder outer surface 211 on the right side of the supply cylinder 21a.

Figure 13:
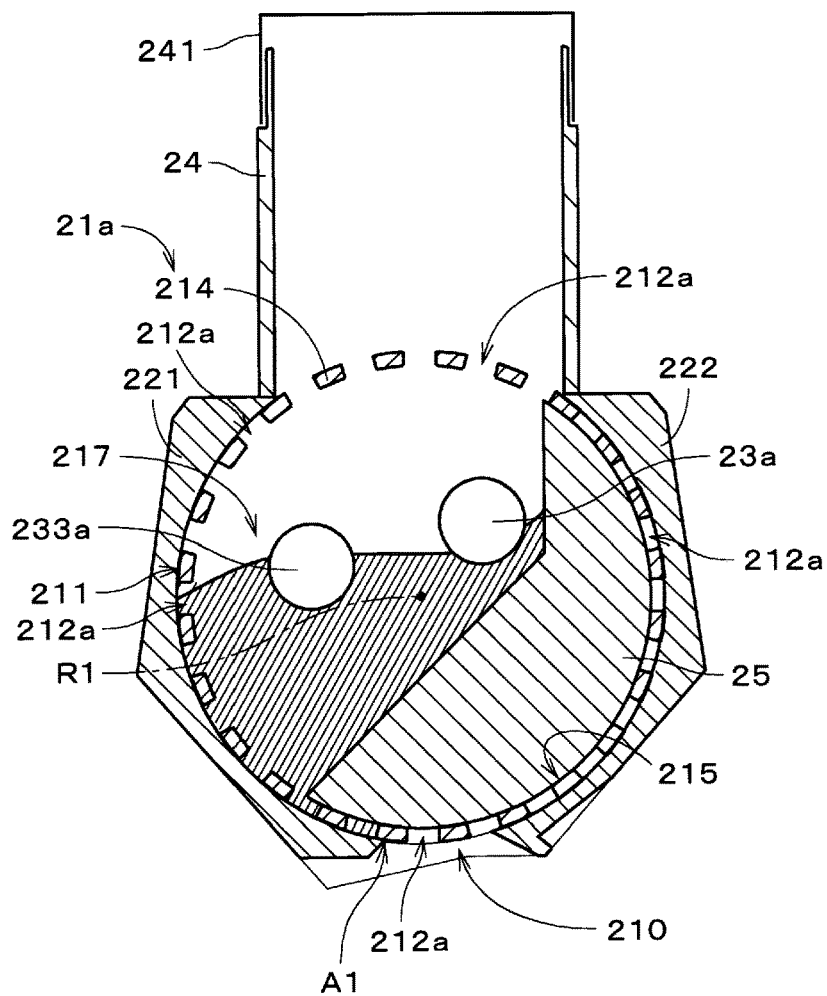
FIG. 13 is a cross-sectional view of the supply cylinder and other constituent elements.
Figure 14:
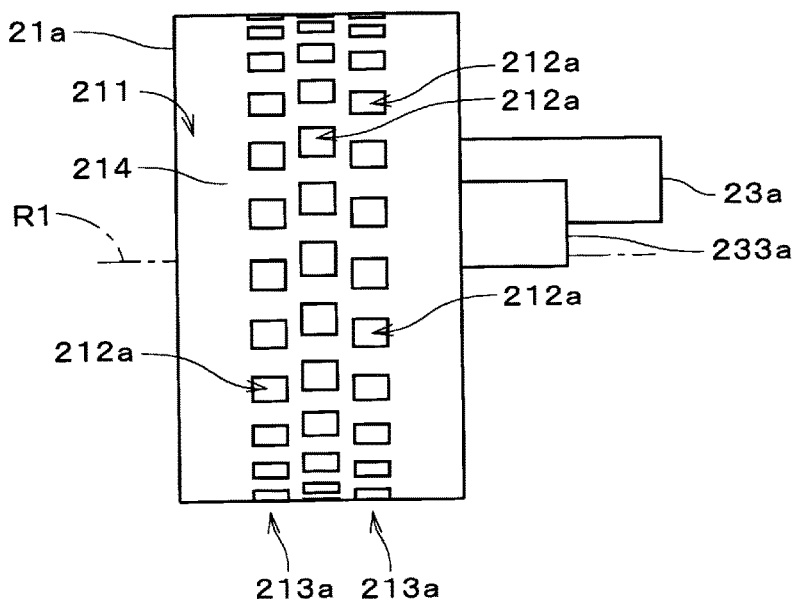
FIG. 14 is a front view of the supply cylinder.

FIG. 13 is an enlarged cross-sectional view of the vicinity of the supply cylinder 21a. FIG. 14 illustrates the cylinder outer surface 211 of the supply cylinder 21a as viewed in a direction perpendicular to the cylinder rotation axis R1. Illustration of the first cover part 221 and the second cover part 222 is omitted in FIG. 14.

As illustrated in FIGS. 13 and 14, the supply cylinder 21a has a plurality of supply holes (hereinafter, the supply holes are referred to as "through holes 212a") that pass through a side wall 214. The plurality of through holes 212a are arrayed circumferentially about the cylinder rotation axis R1 at equal intervals and at a plurality of positions in the axial direction. When a plurality of through holes 212a that are arrayed circumferentially at the same position in the axial direction are referred to as a "through hole row 213a," the supply cylinder 21a includes three through hole rows 213a (i.e., supply hole rows) as illustrated in FIG. 14. In the present embodiment, each through hole 212a has a generally rectangular shape, but the through holes 212a may have various shapes (e.g., approximately circular shapes). The supply cylinder 21a may include one, two, or four or more through hole rows 213a. Each through hole row 213a does not necessarily have to have a plurality of through holes 212a arrayed at equal intervals.

As illustrated in FIG. 13, a separating part 25 that covers part of an inner surface 215 of the side wall 214 of the supply cylinder 21a is provided in the internal space of the supply cylinder 21a. The separating part 25 is provided on the right side of the internal space in FIG. 13 and covers an area on the right side of the inner surface 215 from the vicinity of the lowermost part of the supply cylinder 21a to the vicinity of the uppermost portion thereof. The outer surface of the separating part 25 (i.e., the surface facing the inner surface 215 of the supply cylinder 21a) faces the lower end portion of the first cover part 221, the entire particle supply region 210, and the entire second cover part 222. The upper portion of the inner surface of the separating part 25 is approximately parallel to the direction of gravity, and the lower portion of the inner surface is inclined downward to the left in FIG. 13. In other words, the lower portion of the inner surface of the separating part 25 extends downward in the direction of gravity and linearly approaches the lower part of the first cover part 221. Note that the lower portion of the inner surface of the separating part 25 may be a curved surface that is raised downwardly or upwardly.

An area of the internal space of the supply cylinder 21a where the separating part 25 is not provided is a particle-housing space 217 for housing highly absorbent resin particles. In FIG. 13, the particles are finely diagonally hatched. Since, as described above, the lower portion of the inner surface of the separating part 25 extends downward and approaches the lower part of the first cover part 221, particles in the particle-housing space 217 move along the inner surface of the separating part 25 toward the inner surface 215 of the supply cylinder 21a. The separating part 25 extends approximately across the entire axial width of the inner surface 215 of the supply cylinder 21a, and the particle-housing space 217 and the through holes 212a are separated from each other in a region where the inner surface 215 is covered by the separating part 25. Accordingly, the particle-housing space 217 and the through hole 212a are also separated from each other at the lower part of the supply cylinder 21a where the particle supply region 210 is present.

As illustrated in FIGS. 13 and 14, the absorbent sheet manufacturing apparatus 1b includes a particle filling part 23a on the right side of the supply cylinder 21a in FIG. 14. The particle filling part 23a is a screw feeder having a screw therein and replenishes the particle-housing space 217 of the supply cylinder 21a with particles from one end (right-side end in FIG. 14) in the axial direction of the supply cylinder 21a. The particle-housing space 217 includes a light-receiving, ultrasonic, or contact-type level sensor 233a, and the particle-housing space 217 is replenished with particles when the amount of particles in the particle-housing space 217 is less than or equal to a certain amount. When the particle-housing space 217 illustrated in FIG. 13 is replenished with particles, air in the particle-housing space 217 is exhausted primarily through the exhaust part 24. Note that even if particles jump out of the supply cylinder 21a into the exhaust part 24, the filter 241 prevents the particles from jumping out of the absorbent sheet manufacturing apparatus 1b.

In the absorbent sheet manufacturing apparatus 1b, the supply cylinder 21a rotates at a high speed about the cylinder rotation axis R1, and through holes 212a that face the particles in the particle-housing space 217 among the plurality of through holes 212a of the supply cylinder 21a are filled with the particles in the particle-housing space 217. The outer sides of the through holes 212a are covered by the first cover part 221 (i.e., the through holes 212a are covered from the cylinder outer surface 211 side) until when the through holes 212a filled with particles reach the particle supply region 210 provided at the lower part of the supply cylinder 21a. Particles in each through hole 212a move to a position where the through hole 212 faces the separating part 25 and are thereby isolated from the particles in the particle-housing space 217.

Then, when each through hole 212a passes over the edge of the first cover part 221 in the vicinity of the lowermost part of the supply cylinder 21a, i.e., the front edge of the first cover part 221 in the rotation direction of the supply cylinder 21a, and through the particle supply region 210, particles filled in the through hole 212a are emitted to the outside of the supply cylinder 21a. More specifically, the emission of particles from the supply cylinder 21a starts at the instant when the through holes 212a pass over the above edge of the first cover part 221 (i.e., the emission start position A1). As described previously, the supply cylinder 21a rotates at a high speed, and particles are emitted forward in the rotation direction of the supply cylinder 21a from each of the plurality of through holes 212a approximately along a tangent to the cylinder outer surface 211.

Figure 15:
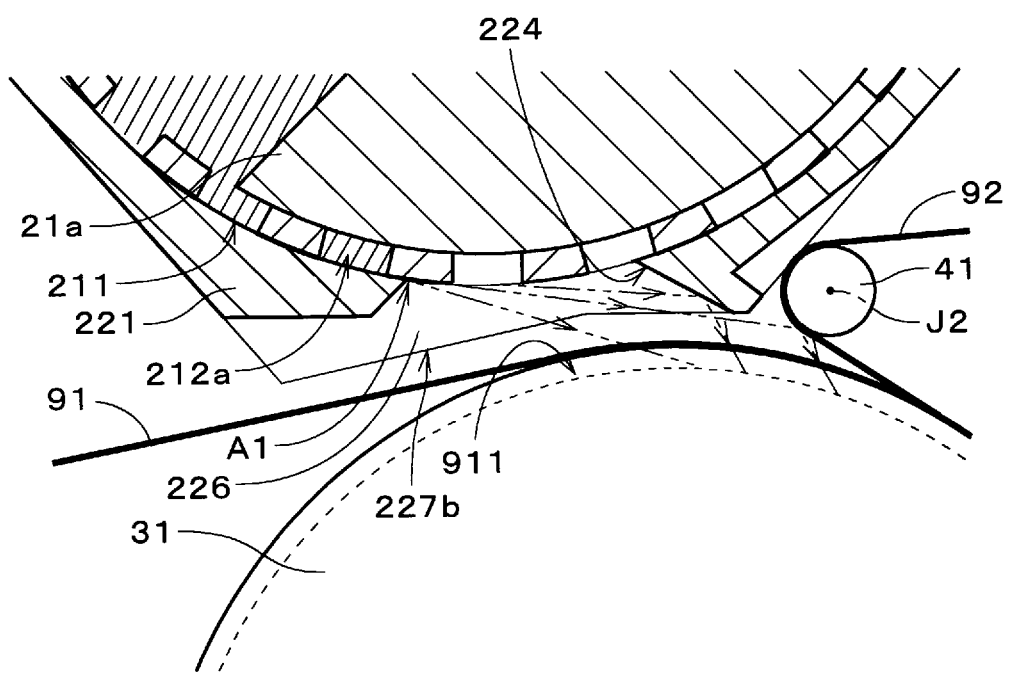
FIG. 15 is a cross-sectional view of the supply cylinder and other constituent elements.

FIG. 15 illustrates how particles are emitted from the supply cylinder 21a. As illustrated in FIG. 15, particles that are emitted approximately at the emission start position A1 are supplied directly to the groove portions 911 of the first sheet member 91 on the first sheet conveying roller 31. Particles that are emitted from the through holes 212a at a slight delay after having passed the emission start position A1 pass between the first sheet member 91 on the first sheet conveying roller 31 and the lower end of the particle collision surface 224 and collide directly with the second sheet member 92 on the second sheet conveying roller 41. The particles then bounce back off the second sheet member 92 and are supplied to the groove portions 911 of the first sheet member 91. Particles that are emitted at a further delay from the through holes 212a collide directly with the particle collision surface 224 that extends downward from the cylinder outer surface 211 in between the lowermost part of the supply cylinder 21a and the second sheet conveying roller 41, bounce back off the particle collision surface 224, and are supplied to the groove portions 911 of the first sheet member 91 that is being conveyed under the particle collision surface 224.

As described above, in the absorbent sheet manufacturing apparatus 1b, as in the absorbent sheet manufacturing apparatus 1 illustrated in FIG. 1, some of the particles emitted forward in the rotation direction of the supply cylinder 21a from the through holes 212a that have passed the first cover part 221 illustrated in FIG. 15 collide with the particle collision surface 224, and the colliding particles are guided by the particle collision surface 224 to the first sheet member 91. It is thus possible to reduce the possibility that particles emitted from the supply cylinder 21a will collide directly with the second sheet member 92 on the second sheet conveying roller 41 and scatter around the first sheet member 91 and the second sheet member 92. This results in efficient supply of particles from the supply cylinder 21a to the first sheet member 91.

In the absorbent sheet manufacturing apparatus 1b, the lower end of the particle collision surface 224 is located below or at the same position as the second central axis J2 of the second sheet conveying roller 41 in the up-down direction. Thus, particles emitted from the through holes 212a that have passed the first cover part 221 toward the space between the lower end of the particle collision surface 224 and the first sheet member 91 on the first sheet conveying roller 31 collide directly with the second sheet member 92 on the second sheet conveying roller 41 at positions below the second central axis J2 of the second sheet conveying roller 41. Thus, particles emitted from the supply cylinder 21a are prevented from colliding directly with the second sheet member 92 on the second sheet conveying roller 41 at positions above the second central axis J2. This further suppresses scattering of particles that have collided with the second sheet member 92 in the surroundings.

The particle collision surface 224 is an inclined surface that is inclined forward in the rotation direction of the supply cylinder 21 with respect to a vertically downward direction. This reduces the impact when particles collide with the particle collision surface 224. Consequently, particles that have collided with the particle collision surface 224 can be guided to the first sheet member 91 while suppressing scattering of the particles in the surroundings. The particle collision surface 224 is also inclined forward in the rotation direction of the supply cylinder 21 with respect to a plane that includes the cylinder rotation axis R1 of the supply cylinder 21 and the upper end edge of the particle collision surface 224. This further suppresses scattering of particles that have collided with the particle collision surface 224 in the surroundings.

Like the absorbent sheet manufacturing apparatus 1 illustrated in FIG. 1, the absorbent sheet manufacturing apparatus 1b includes a pair of side wall parts 226 disposed on both axial sides of the group of through holes 212a (i.e., the group of supply holes) of the cylinder outer surface 211 that are exposed between the lower end of the first cover part 221 and the particle collision surface 224. Each side wall part 226 is provided in close proximity to the cylinder outer surface 211 and continuously from the lower end of the first cover part 221 to the particle collision surface 224, and extends downward from the cylinder outer surface 211. This allows particles to be guided to the first sheet member 91 while suppressing wide sideways scattering of particles that are emitted from the through holes 212a or that have collided with the first roller outer surface 311 (in particular, raised portions on both sides of the annular grooves 312) of the first sheet conveying roller 31 and bounced back. In addition, the lower end of each side wall part 226 of the pair includes the inclined portion 227b that is inclined downward as it extends from the particle collision surface 224 toward the first cover part 221. This suppresses sideways scattering of particles even if the supply cylinder 21a rotates at a relatively low speed.

The first cover part 221, the particle collision surface 224, and the pair of side wall parts 226 are included in an integral member. This eliminates the need, when manufacturing the absorbent sheet manufacturing apparatus 1b, to assemble a plurality of components that correspond respectively to the first cover part 221, the particle collision surface 224, and the pair of side wall parts 226 and accordingly facilitates the manufacture of the absorbent sheet manufacturing apparatus 1b.

Like the absorbent sheet manufacturing apparatus 1a illustrated in FIG. 9, the absorbent sheet manufacturing apparatus 1b may include two partition parts 228 (see FIG. 9) between the pair of side wall parts 226 in the axial direction, the partition parts 228 facing areas of the cylinder outer surface 211 between the plurality of recessed supply portion rows 213. This suppresses sideways scattering of particles emitted from the through holes 212a included in each through hole row 213a. Accordingly, the absorbent sheet 95 as illustrated in FIG. 8 in which the plurality of particle existence regions 951 are formed in distinct strips can be readily manufactured.

The lower end of each partition part 228 may include the inclined portion 229b (see FIG. 9) that is inclined downward as it extends from the particle collision surface 224 toward the first cover part 221. In this case, sideways scattering of particles emitted from each through hole row 213a can be suppressed even if the supply cylinder 21a rotates at a relatively low speed.

The above-described absorbent sheet manufacturing apparatuses 1, 1a, and 1b can be modified in various ways.

For example, in the absorbent sheet manufacturing apparatus 1 illustrated in FIG. 1, the particle filling opening 232 does not necessarily have to face the area including the uppermost portion of the supply cylinder 21 if the recessed supply portions 212 are filled with particles in sufficiently high density, and may be disposed to face a position forward or backward of the uppermost portion of the supply cylinder 21 in the rotation direction of the supply cylinder 21. The absorbent sheet manufacturing apparatus 1b illustrated in FIG. 12 may use, as the particle filling part 23a, an air feeder for conveying a material with compressed air, instead of a screw feeder.

The second sheet conveying roller 41 may have annular grooves that extend circumferentially about the second central axis J2 at each of a plurality of positions in the axial direction of the second roller outer surface 411. The plurality of annular grooves are disposed at the same positions as the positions of the plurality of recessed supply portion rows 213 of the supply cylinder 21 or the plurality of through hole rows 213 of the supply cylinder 21a in the axial direction. The areas of the second sheet member 92 where annular grooves are present are not in contact with the second roller outer surface 411 (i.e., spaced above the second roller outer surface 411). The second sheet member 92 can thus absorb the impact to some extent when particles emitted from each recessed supply portion 212 or each through hole 212a toward the second sheet member 92 collide with the second sheet member 92. This suppresses scattering of particles that have collided with the second sheet member 92 in the surroundings.

The particle collision surface 224 is not necessarily limited to a planar surface, and for example, may be a curved surface that is raised forward in the rotation direction of the supply cylinder 21 or 21a in the middle part of the axial range where the plurality of recessed supply portion rows 213 or the plurality of through hole rows 213 are formed. Alternatively, the particle collision surface 224 may be a wavy curved surface that is raised forward in the rotation direction of the supply cylinder 21 or 21a in the area that corresponds to each recessed supply portion row 213 or each through hole row 213.

The lower end of the particle collision surface 224 may be located above the second central axis J2 of the second sheet conveying roller 41. Even in this case, if particles emitted from the recessed supply portions 212 or the through holes 212a that have passed the first cover part 221 to the space between the lower end of the particle collision surface 224 and the first sheet member 91 on the first sheet conveying roller 31 collide directly with the second sheet member 92 on the second sheet conveying roller 41 at positions below the second central axis J2, it is possible to further suppress scattering of the particles that have collided with the second sheet member 92 in the surroundings.

The first cover part 221, the front wall part 223 having the particle collision surface 224, and the pair of side wall parts 226 do not necessarily have to be included in an integral member. The front wall part 223 may be provided independently of the second cover part 222.

While the above embodiments describe the manufacture of the absorbent sheet 95 in which the particle existence regions 951 are formed in strips, an absorbent sheet having dot-like particle existence regions may, for example, be formed by increasing the circumferential intervals of the plurality of recessed supply portions 212 of the supply cylinder 21 or by increasing the circumferential intervals of the plurality of through holes 212a of the supply cylinder 21a.

The configurations of the absorbent sheet manufacturing apparatuses 1, 1a, and 1b may be applied to absorbent-article sheet member manufacturing apparatuses for manufacturing deodorant sheets by supplying particles of a deodorant material, instead of particles of an absorbent material, to the first sheet member 91. As particles of the deodorant material, the apparatuses use particles of, for example, activated carbon, silica, alumina, zeolite, an ion-exchange resin, or molecular sieve. The deodorant sheets are used in absorbent articles such as disposable diapers or absorbent pads for light incontinence.

The configurations of the above-described preferred embodiments and variations may be appropriately combined as long as there are no mutual inconsistencies.

While the invention has been shown and described in detail, the foregoing description is in all aspects illustrative and not restrictive. It is therefore to be understood that numerous modifications and variations can be devised without departing from the scope of the invention.

REFERENCE SIGNS LIST 1, 1a, 1b Absorbent sheet manufacturing apparatus
21, 21a Supply cylinder
23 Particle filling part
25 Separating part
31 First sheet conveying roller
41 Second sheet conveying roller
51 Bonding roller
91 First sheet member
92 Second sheet member
211 Cylinder outer surface
212 Supply recessed portion
212a Through hole
213 Supply recessed portion row
213a Through hole row
215 Inner surface (of supply cylinder)
217 Particle-housing space
221 First cover part
224 Particle collision surface
226 Side wall part
227 Lower end surface (of side wall part)
227b Inclined portion
228 Partition part
229 Lower end surface (of partition part)
229b Inclined portion
232 Particle filling opening
311 First roller outer surface
411 Second roller outer surface
J1 First central axis
J2 Second central axis
R1 Cylinder rotation axis

The invention claimed is:

1. An absorbent-article sheet member manufacturing apparatus comprising:
a supply cylinder having a cylinder outer surface that is a generally cylindrical surface centered on a rotation axis oriented in a horizontal direction, having a plurality of supply holes that are a plurality of recessed supply portions arrayed in a circumferential direction in said cylinder outer surface, and for rotating about said rotation axis in a predetermined rotation direction;
a particle filling part for housing particles of an absorbent material or a deodorant material above said supply cylinder and successively filling said plurality of supply holes with particles through a particle filling opening that faces said cylinder outer surface;
a half cover part that extends from said particle filling opening to a lower part of said supply cylinder in said rotation direction to cover part of said cylinder outer surface of said supply cylinder;
a first sheet conveying roller disposed below said supply cylinder and in close proximity to a lowermost part of said supply cylinder, said first sheet conveying roller having a first roller outer surface that is a generally cylindrical surface centered on a first central axis oriented in an axial direction that is parallel to said rotation axis, and for rotating about said first central axis in an opposite direction to said rotation direction to convey a first sheet member that is a continuous sheet along said first roller outer surface;
a second sheet conveying roller disposed forward of said lowermost part of said supply cylinder in said rotation direction and in close proximity to said supply cylinder and said first sheet conveying roller, said second sheet conveying roller having a second roller outer surface that is a generally cylindrical surface centered on a second central axis oriented in said axial direction, and for rotating about said second central axis in the same direction as said rotation direction to convey a second sheet member that is a continuous sheet along said second roller outer surface and to layer said second sheet member on said first sheet member;

a particle collision surface that extends from said cylinder outer surface in between said lowermost part of said supply cylinder and said second sheet conveying roller, and that is separated rearwardly from said second sheet conveying roller in said rotation direction, said particle collision surface being disposed so as to collide with some of said particles that are emitted forward in said rotation direction of said supply cylinder from said supply holes that have passed said half cover part and to guide the colliding particles onto said first sheet member; and a sheet bonding part for bonding said first sheet member, on which particles are supplied from said supply cylinder, to said second sheet member, which is layered on said first sheet member by said second sheet conveying roller, wherein said particle collision surface is an inclined surface that is inclined forward in said rotation direction with respect to a vertically downward direction across the entire surface of said particle collision surface.

2. The absorbent-article sheet member manufacturing apparatus according to claim 1, wherein a lower end of said particle collision surface extends downward to at least the same position as said second central axis of said second sheet conveying roller in an up-down direction, and wherein said particles that are emitted from said supply holes that have passed said half cover part toward a space between a lower end of said particle collision surface and said first sheet member on said first sheet conveying roller collide directly with said second sheet member on said second sheet conveying roller at a position below said second central axis of said second sheet conveying roller.

3. The absorbent-article sheet member manufacturing apparatus according to claim 1, wherein a lower end of said particle collision surface is located below or at the same position as said second central axis of said second sheet conveying roller in an up-down direction.

4. The absorbent-article sheet member manufacturing apparatus according to claim 1, further comprising:

a pair of side wall parts disposed on both sides, in said axial direction, of a group of supply holes in said cylinder outer surface that are exposed between a lower end of said half cover part and said particle collision surface, wherein each side wall part of said pair is provided in close proximity to said cylinder outer surface and continuously from said lower end of said half cover part to said particle collision surface, and extends downward from said cylinder outer surface.

5. The absorbent-article sheet member manufacturing apparatus according to claim 4, wherein a lower end of each side wall part of said pair includes an inclined portion that is inclined downward as said inclined portion extends from said particle collision surface toward said half cover part.

6. The absorbent-article sheet member manufacturing apparatus according to claim 4, wherein said plurality of supply holes include a plurality of supply hole rows, each supply hole row being a group of supply holes that are arrayed in said circumferential direction at the same position in said axial direction, said absorbent-article sheet member manufacturing apparatus further comprising:

a partition part provided between said pair of side wall parts and continuously from said lower end of said half cover part to said particle collision surface, wherein said partition part is provided in close proximity to said cylinder outer surface while facing a portion of said cylinder outer surface between said plurality of supply hole rows, and extends downward from said cylinder outer surface.

7. The absorbent-article sheet member manufacturing apparatus according to claim 6, wherein a lower end of said partition part includes an inclined portion that is inclined downward as said inclined portion extends from said particle collision surface toward said half cover part.

8. The absorbent-article sheet member manufacturing apparatus according to claim 1, further comprising a pair of side wall parts disposed on both sides, in said axial direction, of a group of supply holes in said cylinder outer surface that are exposed between a lower end of said half cover part and said particle collision surface, wherein said half cover part, said particle collision surface, and said pair of side wall parts are included in an integral member.

9. The absorbent-article sheet member manufacturing apparatus according to claim 1, wherein said second central axis of said second sheet conveying roller is located at a position that is forward of said lowermost part of said supply cylinder in said rotation direction and between said cylinder outer surface and the first roller outer surface that face each other in an up-down direction.

10. An absorbent-article sheet member manufacturing apparatus comprising:

a supply cylinder that is a generally cylindrical member centered on a rotation axis pointing in a horizontal direction, having a particle-housing space in which part of an internal space is for housing particles of an absorbent material or a deodorant material, having a plurality of supply holes that are a plurality of through holes arrayed in a circumferential direction, and for rotating about said rotation axis in a predetermined rotation direction to fill a supply hole that faces particles housed in said particle-housing space among said plurality of supply holes, with particles a half cover part that extends from a lower part of said supply cylinder in an opposite direction to said rotation direction to cover part of a cylinder outer surface that is an outer surface of said supply cylinder;

a separating part that covers part of an inner surface of said supply cylinder to separate said particle-housing space and a supply hole at said lower part of said supply cylinder;

a first sheet conveying roller disposed below said supply cylinder and in close proximity to a lowermost part of said supply cylinder, having a first roller outer surface that is a generally cylindrical surface centered on a first central axis pointing in an axial direction that is parallel to said rotation axis, and for rotating about said first central axis in an opposite direction to said rotation direction to convey a first sheet member that is a continuous sheet along said first roller outer surface;

a second sheet conveying roller disposed forward of said lowermost part of said supply cylinder in said rotation direction and in close proximity to said supply cylinder and said first sheet conveying roller, having a second roller outer surface that is a generally cylindrical surface centered on a second central axis pointing in said axial direction, and for rotating about said second central axis in the same direction as said rotation direction to convey a second sheet member that is a continuous sheet along said second roller outer surface and to layer said second sheet member on said first sheet member;

a particle collision surface that extends from said cylinder outer surface in between said lowermost part of said supply cylinder and said second sheet conveying roller, and for colliding with some of said particles that are emitted forward in said rotation direction of said supply cylinder from a supply hole that has passed said half cover part and guiding the colliding particles onto said first sheet member; and a sheet bonding part for bonding said first sheet member and said second sheet member to each other.

11. The absorbent-article sheet member manufacturing apparatus according to claim 10, wherein
said particle collision surface is an inclined surface that is inclined forward in said rotation direction with respect to a vertically downward direction.

12. The absorbent-article sheet member manufacturing apparatus according to claim 10, wherein
said particles that are emitted from said supply hole that has passed said half cover part toward a space between a lower end of said particle collision surface and said first sheet member on said first sheet conveying roller collide directly with said second sheet member on said second sheet conveying roller at a position below said second central axis of said second sheet conveying roller.

13. The absorbent-article sheet member manufacturing apparatus according to claim 10, wherein
a lower end of said particle collision surface is located below or at the same position as said second central axis of said second sheet conveying roller in an up-down direction.

14. The absorbent-article sheet member manufacturing apparatus according to claim 10, further comprising:
a pair of side wall parts disposed on both sides, in said axial direction, of a group of supply holes in said cylinder outer surface that are exposed between a lower end of said half cover part and said particle collision surface,
wherein each side wall part of said pair is provided in close proximity to said cylinder outer surface and continuously from said lower end of said half cover part to said particle collision surface, and extends downward from said cylinder outer surface.

15. The absorbent-article sheet member manufacturing apparatus according to claim 14, wherein
a lower end of each side wall part of said pair includes an inclined portion that is inclined downward as said inclined portion extends from said particle collision surface toward said half cover part.

16. The absorbent-article sheet member manufacturing apparatus according to claim 14, wherein
said half cover part, said particle collision surface, and said pair of side wall parts are included in an integral member.

17. The absorbent-article sheet member manufacturing apparatus according to claim 14, wherein
said plurality of supply holes include a plurality of supply hole rows, each supply hole row being a group of supply holes that are arrayed in said circumferential direction at the same position in said axial direction,
said absorbent-article sheet member manufacturing apparatus further comprising:
a partition part provided between said pair of side wall parts and continuously from said lower end of said half cover part to said particle collision surface,
wherein said partition part is provided in close proximity to said cylinder outer surface while facing a portion of said cylinder outer surface between said plurality of supply hole rows, and extends downward from said cylinder outer surface.

18. The absorbent-article sheet member manufacturing apparatus according to claim 17, wherein
a lower end of said partition part includes an inclined portion that is inclined downward as said inclined portion extends from said particle collision surface toward said half cover part.

19. The absorbent-article sheet member manufacturing apparatus according to claim 10, wherein
said second central axis of said second sheet conveying roller is located at a position that is forward of said lowermost part of said supply cylinder in said rotation direction and between said cylinder outer surface and the first roller outer surface that face each other in an up-down direction.

* * * * *